(12) United States Patent
Dosier et al.

(10) Patent No.: US 12,187,620 B2
(45) Date of Patent: *Jan. 7, 2025

(54) BIOCEMENTATION METHOD AND SYSTEM

(71) Applicant: Biomason Inc., Durham, NC (US)

(72) Inventors: Ginger K. Dosier, Raleigh, NC (US); John Michael Dosier, Raleigh, NC (US); Kent J. Smith, Durham, NC (US)

(73) Assignee: Biomason Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/052,066

(22) Filed: Nov. 2, 2022

(65) Prior Publication Data

US 2023/0202859 A1    Jun. 29, 2023

Related U.S. Application Data

(63) Continuation of application No. 16/153,374, filed on Oct. 5, 2018, now Pat. No. 11,518,687.

(60) Provisional application No. 62/568,539, filed on Oct. 5, 2017, provisional application No. 62/735,060, filed on Sep. 22, 2018, provisional application No. 62/577,911, filed on Oct. 27, 2017.

(51) Int. Cl.

| | |
|---|---|
| *C01F 11/06* | (2006.01) |
| *C01F 11/18* | (2006.01) |
| *C01F 11/24* | (2006.01) |
| *C04B 12/00* | (2006.01) |
| *C04B 14/22* | (2006.01) |
| *C04B 14/28* | (2006.01) |
| *C04B 18/12* | (2006.01) |
| *C04B 18/16* | (2023.01) |
| *C04B 22/00* | (2006.01) |
| *C04B 28/10* | (2006.01) |
| *C04B 103/00* | (2006.01) |
| *C12P 3/00* | (2006.01) |

(52) U.S. Cl.
CPC ............. *C01F 11/06* (2013.01); *C01F 11/18* (2013.01); *C01F 11/24* (2013.01); *C04B 12/00* (2013.01); *C04B 14/22* (2013.01); *C04B 14/28* (2013.01); *C04B 18/12* (2013.01); *C04B 18/16* (2013.01); *C04B 22/0026* (2013.01); *C04B 28/10* (2013.01); *C12P 3/00* (2013.01); *C04B 2103/0001* (2013.01); *C04B 2103/001* (2013.01)

(58) Field of Classification Search
CPC ........... C01F 11/06; C01F 11/18; C01F 11/24; C04B 12/00; C04B 14/22; C04B 14/28; C04B 18/12; C04B 18/16; C04B 22/0026; C04B 2103/0001; C04B 2103/001; C04B 28/10; C04B 20/1018; Y02W 30/91; C12P 3/00

See application file for complete search history.

(56) References Cited

U.S. PATENT DOCUMENTS

| | | |
|---|---|---|
| 3,667,976 A | 6/1972 | Tanner et al. |
| 3,829,553 A | 8/1974 | Lynn |
| 4,204,876 A | 5/1980 | Bowden |
| 4,617,326 A | 10/1986 | Bjornberg et al. |
| 4,946,505 A | 8/1990 | Jungk |
| 5,143,155 A | 9/1992 | Ferris et al. |
| 5,199,986 A | 4/1993 | Krockert et al. |
| 5,558,708 A | 9/1996 | Johansen, Jr. et al. |
| 5,846,315 A | 12/1998 | Johansen, Jr. et al. |
| 5,891,205 A | 4/1999 | Picardi et al. |
| 6,348,147 B1 | 2/2002 | Long |
| 7,025,824 B2 | 4/2006 | Axen et al. |
| 7,101,430 B1 | 9/2006 | Pike et al. |
| 8,182,604 B2 | 5/2012 | Kucharski et al. |
| 8,420,362 B2 | 4/2013 | Crawford et al. |
| 8,470,275 B2 | 6/2013 | Constantz et al. |
| 8,518,177 B2 | 8/2013 | Chattopadhyay et al. |
| 8,728,365 B2 | 5/2014 | Dosier |
| 8,911,549 B2 | 12/2014 | Jonkers |

(Continued)

FOREIGN PATENT DOCUMENTS

| | | |
|---|---|---|
| CA | 2591097 A1 | 6/2006 |
| CN | 1285401 A | 2/2001 |

(Continued)

OTHER PUBLICATIONS

Botusharova SP., Self-Healing Geotechnical Structures via Microbial Action. PhD., Thesis, Cardiff Univ., UK, 2017, pp. 1-234. (Year: 2017).*

Dhami et al., Bacterial Community Dynamics and Biocement Formation during Stimulation and Augmentation: Implications for Soil Consolidation. Frontiers Microbiol., 2017, Article 1267, pp. 1-17. (Year: 2017).*

Parmar et al., Bio Cementation: A Novel Technique and Approach Towards Sustainable Material. World J Res. Rev., 2017, vol. 4(3): 36-41. (Year: 2017).*

(Continued)

*Primary Examiner* — Ganapathirama Raghu
(74) *Attorney, Agent, or Firm* — Tyler Thorp; Newport IP, LLC

(57) ABSTRACT

The invention is directed to kits, compositions, tools and methods comprising a cyclic industrial process to form biocement. In particular, the invention is directed to materials and methods for decomposing calcium carbonate into calcium oxide and carbon dioxide at an elevated temperature, reacting calcium oxide with ammonium chloride to form calcium chloride, water, and ammonia gas; and reacting ammonia gas and carbon dioxide at high pressure to form urea and water, which are then utilized to form biocement. This cyclic process can be achieved by combining industrial processes with the resulting product as biocement. The process may involve retention of calcium carbonate currently utilized in the manufacture of Portland Cement.

16 Claims, 6 Drawing Sheets

(56) References Cited

U.S. PATENT DOCUMENTS

| | | |
|---|---|---|
| 8,912,244 B2 | 12/2014 | Vitomir et al. |
| 8,932,400 B2 | 1/2015 | Chen et al. |
| 8,951,786 B1 | 2/2015 | Dosier |
| 9,074,134 B2 | 7/2015 | Bang et al. |
| 9,199,880 B2 | 12/2015 | Dosier |
| 9,428,418 B2 | 8/2016 | Dosier |
| 9,796,626 B2 | 10/2017 | Dosier |
| 10,125,303 B2 | 11/2018 | Wilson et al. |
| 10,450,695 B2 | 10/2019 | Dosier et al. |
| 10,626,547 B2 | 4/2020 | Dosier et al. |
| 10,717,674 B2 | 7/2020 | Hill et al. |
| 11,008,591 B2 | 5/2021 | Dosier et al. |
| 11,472,738 B2 | 10/2022 | Hill et al. |
| 11,518,687 B2 | 12/2022 | Dosier et al. |
| 2005/0029187 A1 | 2/2005 | Koga et al. |
| 2005/0103204 A1 | 5/2005 | Halliday et al. |
| 2005/0103234 A1 | 5/2005 | McNulty, Jr. |
| 2008/0245272 A1 | 10/2008 | Kucharski et al. |
| 2010/0086367 A1 | 4/2010 | Darson-Baulleur et al. |
| 2010/0210745 A1 | 8/2010 | McDaniel et al. |
| 2011/0011303 A1 | 1/2011 | Jonkers |
| 2011/0027850 A1 | 2/2011 | Crawford et al. |
| 2012/0199046 A1 | 8/2012 | Jonkers |
| 2013/0112114 A1 | 5/2013 | Jonkers |
| 2013/0196419 A1 | 8/2013 | Chavez Crooker et al. |
| 2014/0248681 A1 | 9/2014 | Soens et al. |
| 2014/0369749 A1 | 12/2014 | Friedman et al. |
| 2015/0264898 A1 | 9/2015 | Ortego et al. |
| 2015/0322604 A1 | 11/2015 | Brunner et al. |
| 2016/0010434 A1 | 1/2016 | Portman et al. |
| 2016/0090328 A1 | 3/2016 | Wiktor et al. |
| 2016/0130489 A1 | 5/2016 | Gilmour |
| 2016/0174530 A1 | 6/2016 | Barber |
| 2016/0264463 A1 | 9/2016 | Dosier et al. |
| 2017/0015832 A1 | 1/2017 | Berlin et al. |
| 2017/0190620 A1 | 7/2017 | Jonkers et al. |
| 2018/0118623 A1 | 5/2018 | Smith et al. |
| 2018/0244585 A1 | 8/2018 | Rahbar et al. |
| 2019/0210924 A1 | 7/2019 | Royne et al. |
| 2020/0171533 A1 | 6/2020 | Dosier et al. |
| 2020/0262711 A1 | 8/2020 | Dosier et al. |
| 2020/0346976 A1 | 11/2020 | Hill et al. |
| 2021/0189238 A1 | 6/2021 | Kavazanjian et al. |
| 2021/0395146 A1 | 12/2021 | Dosier et al. |
| 2022/0126317 A1 | 4/2022 | Dosier et al. |

FOREIGN PATENT DOCUMENTS

| | | | |
|---|---|---|---|
| CN | 1807358 A | 7/2006 | |
| CN | 101270369 A | 9/2008 | |
| CN | 101054568 B | 5/2010 | |
| CN | 102587875 A | 7/2012 | |
| CN | 103173376 A | 6/2013 | |
| CN | 103173376 B | 10/2014 | |
| CN | 104071890 A | 10/2014 | |
| CN | 105080932 A | 11/2015 | |
| CN | 105418013 A | 3/2016 | |
| CN | 105837075 A | 8/2016 | |
| CN | 105884308 A | 8/2016 | |
| CN | 105924053 A | 9/2016 | |
| CN | 105925512 A | 9/2016 | |
| EP | 0388304 A1 | 9/1990 | |
| EP | 0631998 A1 | 1/1995 | |
| EP | 1838642 A1 | 10/2007 | |
| EP | 1893546 A1 | 3/2008 | |
| EP | 2082999 A1 | 7/2009 | |
| EP | 2247551 A1 | 11/2010 | |
| EP | 2297062 A1 | 3/2011 | |
| EP | 2429970 A1 | 3/2012 | |
| EP | 2462232 A2 | 6/2012 | |
| EP | 2940122 A1 | 11/2015 | |
| JP | S63227330 A | 9/1988 | |
| JP | H05253908 A | 10/1993 | |
| JP | 2006144285 A | 6/2006 | |
| JP | 2007284974 A | 11/2007 | |
| JP | 2008524096 A | 7/2008 | |
| JP | 2009270302 A | 11/2009 | |
| JP | 2011045333 A | 3/2011 | |
| JP | 2011509915 A | 3/2011 | |
| JP | 2012019751 A | 2/2012 | |
| JP | 2013505705 A | 2/2013 | |
| JP | 2013523590 A | 6/2013 | |
| JP | 5253908 B2 | 7/2013 | |
| JP | 5284646 B2 | 9/2013 | |
| JP | 2014005617 A | 1/2014 | |
| JP | 2014510689 A | 5/2014 | |
| WO | WO-0248069 A1 | 6/2002 | |
| WO | WO-03055450 A1 | 7/2003 | |
| WO | WO-2006066326 A1 | 6/2006 | |
| WO | WO-2007044439 A2 | 4/2007 | |
| WO | WO-2007070706 A2 | 6/2007 | |
| WO | WO-2008009771 A1 | 1/2008 | |
| WO | WO-2008120979 A1 | 10/2008 | |
| WO | WO-2009009838 A1 | 1/2009 | |
| WO | WO-2009093898 A1 | 7/2009 | |
| WO | WO-2010130712 A1 | 11/2010 | |
| WO | WO-2011126361 A1 | 10/2011 | |
| WO | WO-2011137106 A1 | 11/2011 | |
| WO | WO-2012113765 A1 | 8/2012 | |
| WO | WO-2013120847 A1 | 8/2013 | |
| WO | WO-2014185781 A1 | 11/2014 | |
| WO | WO-2015042031 A1 | 3/2015 | |
| WO | WO-2015155769 A1 | 10/2015 | |
| WO | WO-2016010434 A1 | 1/2016 | |
| WO | WO-2016144786 A1 | 9/2016 | |
| WO | WO-2016145190 A1 | 9/2016 | |
| WO | WO-2017139750 A1 | 8/2017 | |
| WO | WO-2017189106 A1 | 11/2017 | |
| WO | WO-2017220768 A1 | 12/2017 | |
| WO | WO-2018064320 A1 | 4/2018 | |
| WO | WO-2018081542 A1 | 5/2018 | |
| WO | WO-2018200684 A1 | 11/2018 | |
| WO | WO-2019071172 A1 | 4/2019 | |
| WO | WO-2019071175 A1 | 4/2019 | |
| WO | WO-2020168342 A1 | 8/2020 | |
| WO | WO-2020180914 A1 | 9/2020 | |
| WO | WO-2020198295 A1 | 10/2020 | |
| WO | WO-2022010915 A1 | 1/2022 | |

OTHER PUBLICATIONS

Achal, Varenyam, et al., "Biogenic Treatment Improves the Durability and Remediates the Cracks of Concrete Structures", Construction and Building Materials, 2013, vol. 48, pp. 1-5.

Application of Bacteria as Self-Healing Agent for the Development of Sustainable Concrete, H.M. Jonkers et al., Ecological Engineering 36:230-235, 2010.

Bang et al., "Calcite precipitation induced by polyurethane immobilized Bacillus pasteurii", Enzyme and Microbial Technology, 2001, vol. 28, pp. 404-409.

BioZEment (completed). Web Page. UiO Department of Physics. Published Nov. 3, 2014. Last modified Nov. 27, 2017. Retrieved Oct. 22, 2021 at URL: https://www.mn.uio.no/fysikk/english/research/projects/biozement/ . 5 pages.

Bundur et al., Biomineralized cement-based materials: impact of inoculating vegetative bacterial cells on hydration and strength. Cement and Concrete Res., 2015, vol. 67: 237-245. Available online Oct. 27, 2014.

Castro-Alonso et al., Microbially Induced Calcium Carbonate Precipitation (MICP) and Its Potential in Bioconcrete: Microbiological and Molecular concepts. Frontiers in Materials, 2019, vol. 6, Article 126: 1-15.

Chekroun et al. Precipitation and Growth Morphology of Calcium Carbonate Induced by Myxococcus Xanthus: Implications for Recognition of Bacterial Carbonates. Journal of Sedimentary Research 74 (6): 868-876 (2004).

Cho et al., "Effect of Surfactants on CO2 Biomineralization with *Sporosarcina pasteurii* and *Bacillus megaterium*", Water Air Soil Pollut., 2015, vol. 226:2245, pp. 1-12.

Choi, Sun-Gyu, et al., "Biocementation for Sand Using an Eggshell as Calcium Source", Journal of Geotech, Journal of Geotechnical and Geoenvironmental Engineering, Technical Note, 2016, pp. 1-4.

(56) References Cited

OTHER PUBLICATIONS

Choi, Sun-Gyu, et al., "Properties of Biocemented, Fiber Reinforced Sand", Construction and Building Materials, 2016, vol. 120, pp. 623-629.
Chu, Jian, et al., "Proof of Concept: Biocement for Road Repair", Final Report, Mar. 2015, Iowa State University, Midwest Transportation Center, 15 Pages.
Chu, Jian, "Solutions to Sustainability in Construction: Some Examples", Procedia Engineering, 2016, vol. 145, pp. 1127-1134.
Cichoż-Lach et al. Current pathogenetic aspects of hepatic encephalopathy and noncirrhotic hyperammonemic encephalopathy. World J Gastroenterol. Jan. 7, 2013;19(1):26-34.
CN201880079054.8 Search Report dated Aug. 19, 2021 (w/ partial English translation).
Co-pending U.S. Appl. No. 16/933,171, inventors Hill; Thomas A. et al., filed Jul. 20, 2020.
Co-pending U.S. Appl. No. 17/822,067, inventors Hill; Thomas A. et al., filed Aug. 24, 2022.
Co-pending U.S. Appl. No. 17/931,295, inventors Dosier; Ginger K. et al., filed Sep. 12, 2022.
Co-pending U.S. Appl. No. 18/149,854, inventors Dosier; John Michael et al., filed Jan. 4, 2023.
Co-pending U.S. Appl. No. 18/178,078, inventors Hill; Thomas A. et al., filed Mar. 3, 2023.
Co-pending U.S. Appl. No. 18/178,082, inventor Dosier; Ginger K., filed Mar. 3, 2023.
Cunningham, A.B., et al., "Reducing the Risk of Well Bore Leakage of $CO_2$ Using Engineered Biomineralization Barriers", Energy Procedia, 2011, vol. 4, pp. 5178-5185.
Cuzman et al., Bacterial "Masons" at work with wastes for producing eco-cement. Int. J. Environ. Sci. Develop., 2015, vol. 6(10): 767-774.
Day, Jeremy L. et al, Microbiologically Induced Sealant for Concrete Crack Remediation, https://www.ce.washingtonedu/em2003/proceedings/papers/352.pdf (2003).
De Muynck, Willem et al, Microbial Carbonate Precipitation in Construction Materials: A Review, Ecological Engineering, 2010, pp. 118-136, vol. 36, Elsevier.
Dejong, Jason T. et al, Bio-mediated Soil Improvement; Ecological Engineering, 2009, pp. 197-210, vol. 36, Elsevier.
Dejong, Jason T. et al, Microbially Induced Cementation to Control Sand Response to Undrained Shear, Journal of Geotechnical and Geoenvironmental Engineering, Nov. 2006, pp. 1381-1392, ASCE.
EP18865006.3 Extended European Search Report dated May 28, 2021.
Examination Report for AU Application No. 2018346776 dated Oct. 23, 2020.
Examination Report for IN Application No. 202017014638 dated Nov. 6, 2020.
F. D. Meyer et al, "Microbiologically-Induced Soil Stabilization: Application of *Sporosarcina pasteurii* for Fugitive Dust Control", GEO-FRONTIERS 2011, Reston, VA, (Mar. 11, 2011), doi:10.1061/41165(397)409, ISBN 978-0-7844-1165-0, pp. 4002-4011, XP055562331.
Ferris, F.G. et al, Bacteriogenic Mineral Plugging, Petroleum Society of CIM and CANMET, Paper No. 11, presented at the CIM/CANMET Fourth Petroleum Conference held in Regina, Sask., pp. 11-1 to 11-12, Oct. 7-9, 1991.
Fritzges, Michael B. et al, Biologically Induced Improvement of Loose Sand, Proceedings of the 8th U.S. National Conference on Earthquake Engineering, Apr. 18-22, 2006, Paper No. 1691, San Francisco, US.
Fujita, Yoshiko, et al., Evaluating the Potential of Native Ureolytic Microbes to Remediate a 90Sr Contaminated Environment, Environmental Science & Technology, 2010, vol. 44, No. 19, pp. 7652-7658.
Fukue et al, Grain growth of carbonates using ureolytic microbes, Japanese Geotechnical Journal, (2011), vol. 6, No. 3, pp. 455-464, with English translation of abstract.

Ghosh, P., et al., "Use of Microorganism to Improve the Strength of Cement Mortar", Cement and Concrete Research, 2005, vol. 35, pp. 1980-1983.
Gleb B. Sukhorukov et al., "Porous calcium carbonate microparticles as templates for encapsulation of bioactive compounds" J. Mater. Chem. 14:2073-2081, 2004.
Gollapudi, U.K. et al, A New Method for Controlling Leaching Through Permeable Channels, Chemosphere, 1995, pp. 695-705, vol. 30, No. 4, Elsevier Science Ltd., Great Britain.
Hammes et al. Key roles of pH and calcium metabolism in microbial carbonate precipitation. Re/Views in Environmental Science & Bio/Technology 1:3-7 (2002).
Ivanov et al, "Calcite/aragonite-biocoated artificial coral reefs for marine parks", AIMS Environmental Science, Aug. 22, 2017, vol. 4 (4), pp. 586-595.
Ivanov et al., Chapter 7, Biocementation and Biocements. Construction Biotechnol., Green Energy and Technol., Chapter 7, 2017, pp. 109-138.
Jonkers, Henk M., et al., "A Two Component Bacteria-Based Self-Healing Concrete", Proceedings of the 2nd International Conference on Concrete Repair, Rehabilitation and Retrofitting (ICCRRR), Cape Town, South Africa, Nov. 24-26, 2008. Concrete Repair, Rehabilitation and Retrofitting II, pp. 119-120, Taylor & Francis Group, London.
JP2020-540691 Search Report dated Jul. 5, 2022 (w/ English translation).
Kalantary et al., Evaluation of the ability to control biological precipitation to improve sandy soils. Procedia Earth. Planet. Sci., 2015, vol. 15:278-284.
Kantzas, A. et al, A Novel Method of Sand Consolidation Through Bacteriogenic Mineral Plugging, Petroleum Society of CIM, Jun. 7-10, 1992, pp. 46-1-46-15, Paper No. CIM 92-46.
Karthik et al. Properties of Bacterial-based Self-healing Concrete—A review. International Journal of ChemTech Research, vol. 9, No. 2, pp. 182-188 (2016).
Kim et al. Calcium Carbonate Precipitation by Bacillus and Sporosarcina Strains Isolated from Concrete and Analysis of the Bacterial Community of Concrete. J. Microbiol. Biotechnol. (2016), 26(3), 540-548. First published online Dec. 23, 2015.
Kim et al. Microbially mediated calcium carbonate precipitation on normal and lightweight concrete. Construction and Building Materials, vol. 38, pp. 1073-1082 (2013). Available online Nov. 6, 2012.
Kurizaki et al, "A Case of Stone Formation in the Mainz Pouch using Appendix as the Efferent Limb: A Case Report", Nihon Hinyokika Gakkai Zasshi. The Japanese Journal of Urology, 2002, vol. 93(4), pp. 573-576. (English translation of abstract.).
Ibtisam A. Hammad et al., Urease activity and induction of calcium carbonate precipitation by Sporosarcina pasteurii NCIMB 8841; Journal of Applied Sciences Research 9(3): 1525-33, 2013.
Le Metayer-Levrel G, et al, "Applications of bacterial carbontogenesis to the protection and regeneration of limestones in building and historic patrimony," Sedimentary Geology, Jul. 31, vol. 126, No. 1, pp. 26, 29, 32-33 (1999).
Mazria. It's the Architecture, Stupid! pp. 48-51. Retrieved Aug. 29, 2021 from URL: https://backspace.com/notes/images/its_the_architecture.pdf . May/Jun. 2003.
Mendz et al. The urea cycle of Helicobacter pylori. Microbiology 142, 2959-2967 (1996).
Metayer-Levrel et al., Applications of bacterial carbonatogenesis to the protection and regeneration of limestones in buildings and historic patrimony. Sedimentary Geology., 1999, vol. 126: 25-34.
Meyer et al., "Microbiologically-Induced Soil Stabilization: Application of Sporosarcina pasteurii for Fugitive Dust Control", Geo-Frontiers Congress 2011, pp. 4002-4011.
Nemati, M. et al, Modification of Porous Media Permeability, Using Calcium Carbonate Produced Enzymatically In Situ, Enzyme and Microbial Technology, 2003, pp. 635-642, vol. 33, Elsevier.
Park et al., "Effect of Plant-Induced Calcite Precipitation on the Strength of Sand", Journal of Materials in Civil Engineering, 2014, vol. 26, Issue 8.
PCT/US2018/054683 International Preliminary Report on Patentability dated Apr. 8, 2020.

(56) References Cited

OTHER PUBLICATIONS

PCT/US2018/054683 International Search Report and Written Opinion dated Dec. 7, 2018.
Pedersen et al. Evidence for bacterial urea production in marine sediments. FEMS Microbiology Ecology 12, 51-59 (1993).
Phillips A.J., Biofilm-induced calcium carbonate precipitation: Application in the subsurface. Ph. D., Dissertation, Montana State University, Nov. 2013, pp. 1-241.
Phillips et al., Engineered applications of ureolytic biomineralization: a review. Biofouling, 2013, vol. 29(6): 715-733.
Phua, Y.J., et al., "Morphology and Polymorphism of Calcium Carbonate Precipitated from Different Calcium Sources via Enzyme Induced Carbonate Precipitation", Department of Physics, University of Oslo, Norway, 2016, Goldschmidt Conference Abstracts—1 Page.
Pinar et al., "Bacterial Community Dynamics During the Application of a *Myxococcus xanthus*—Inoculated Culture Medium Used for Consolidation of Ornamental Limestone", Microb.Ecol., 2010, vol. 60, pp. 15-28.
Reddy et al. Embodied energy of common and alternative building materials and technologies. Energy and Buildings, vol. 35, Issue 2, pp. 129-137 (2003).
Remediation of Concrete Using Microorganisms, S.K. Ramachandran et al., ACI Materials Journal Jan./Feb. 2001.
Rodriguez-Navarro, Carlos, et al., "Influence of Substrate Mineralogy on Bacterial Mineralization of Calcium Carbonate: Implications for Stone Conservation", Applied and Environmental Microbiology, Jun. 2012, vol. 78, No. 11, pp. 4017-4029.
Romillac N., Ammonification. Encyclopedia of Ecology, 2nd edition, 2019, vol. 2: 256-263.
Search and Examination Report for European Patent Application No. 18864089.0 dated Jun. 4, 2021.
Stabnikov et al., "Immobilization of Sand Dust and Associated Pollutants Using Bioaggregation", Water, Air, & Soil Pollution, 2013, vol. 224, 1631.
Stabnikov, Viktor, et al., "Halotolerant, Alkaliphilic Urease-Producing Bacteria from Different Climate Zones and their Application for Biocementation of Sand", World Journal of Microbiology and Biotechnology, 2013, vol. 29, pp. 1453-1460.
Stocks-Fischer, Shannon et al, Microbiological Precipitation of CaCO3, Soil Biology and Biochemistry, 1999, pp. 1563-1571, vol. 31, Elsevier Science Ltd.
Streamer, M., "Urea and Arginine metabolism in the Hard Coral, Acropora acuminata", Comp. Biochem. Physiol., vol. 65B, pp. 669 to 674, 1980.
Sun et al. Study of magnesium precipitation based on biocementation. Marine Georesources & Geotechnology, 2019, vol. 37, No. 10, pp. 1257-1266. Published online Jan. 29, 2019.
Talaiekhozani et al., "Application of Proteus mirabilis and Proteus vulgaris mixture to design self-healing concrete", Desalination and Water Treatment, 2014, vol. 52, pp. 3623-3630.
The Better Brick, 2010 Next Generation Winner (https://www.metropolismag.com/uncategorized/the-better-brick-2010-next-generation-winner/).
Therkildsen et al., Urea production by the marine bacteria *Delaya venusta* and *Pseudomonas stutzeri* grown in minimal medium, Aquatic Microbial Ecology, vol. 13:213-217 (1997).
Through the Sandglass, (http://throughthesandglass.typepad.com/through_the_sandglass/2010/07/sandbacteriaurinebricks-continuing-performances-of-bacillus-pasteurii.html) Jul. 19, 2010.
T.K. Ghose et al., "Studies on fibre-entrapped whole microbial cells in urea hydrolysis," Enzyme and Microbial Technology, vol. 1, No. 1, pp. 47-50, Jan. 1, 1979.
U.S. Appl. No. 16/153,374 Office Action dated Mar. 4, 2021.
U.S. Appl. No. 16/153,374 Office Action dated Mar. 7, 2022.
U.S. Appl. No. 16/153,374 Notice of Allowance dated Aug. 11, 2022.
U.S. Appl. No. 16/153,374 Office Action dated Jun. 15, 2021.
Van Paassen et al. Scale up of BioGrout: a biological ground reinforcement method. Hamza et al., ed. Proceedings of the 17th International Conference on Soil Mechanics and Geotechnical Engineering, IOS Press, pp. 2328-2333 (2009).
Van Paassen, Leon A., et al., "Potential Soil Reinforcement by Biological Denitrification", Ecological Engineering, 2010, vol. 36, pp. 168-175.
Vijay et al. Bacteria based self healing concrete—A review. Construction and Building Materials 152:1008-1014 (2017). Available online Jul. 15, 2017.
Wang et al., Application of microorganisms in concrete: a promising sustainable strategy to improve concrete durability. Appl. Microbial Biotechnol., 2016, vol. 100: 2993-3007.
Wei et al. Biomineralization processes of calcite induced by bacteria isolated from marine sediments. Brazilian Journal of Microbiology 46, 2, 455-464 (2015).
Whiffin. Victoria S. et al., Microbial Carbonate Precipitation as a Soil Improvement Technique, Geomicrobiology Journal, 2007, pp. 417-423, vol. 24, Taylor & Francis Group, LLC.
Whiffin, Victoria S., Microbial CaCO3 Precipitation for the Production of Biocement, PhD Thesis, 2004, Murdoch University, Western Australia.
Wikipedia, "Shale," Aug. 22, 2018; retrieved on Sep. 13, 2021 from https://en.wikipedia.org/w/index.php?title=Shale&oldid=855968675.
Wikipedia, "Pseudomonas fluorescens," May 15, 2018; retrieved on Sep. 13, 2021 from https://en.wikipedia.org/w/index.php?title-Pseudomonas_fluorescens&oldid=841444300.
Wiktor et al., Quantification of crack-healing in novel bacteria-based self-healing concrete. Cement & Concrete Composites, 2011, vol. 33: 763-770.
Yoosathaporn et al., The influence of biocalcification on soil-cement interlocking block compressive strength. Biotechnol. Agron. Soc. Environ.,2015, vol. 19 (3): 262-269.
Zander, R., et al., "Association Between Plasma Ionized Calcium and Lactate Concentration", Intensive Care Medicine, 1993, vol. 19, No. 6, pp. 362-363.
Zeolite as a Binding Agent for Ammonia Ions and as a Soil Additive. Part 1 Amonnia Adsorption by the Zeolite, Proceedings of the 5th Serbian-Croatian-Slovenian Symposium on Zeolites, J. Milovanovic et al., May 2013.
Zeynep Basaran Bundur et al., Biomineralized cement-based materials: Impact of inoculating vegetative bacterial cells on hydration and strength, Cement and Concrete Research 67:237-245 (2015). (Available online Oct. 27, 2014).
Zhao et al., Bioremediation of Cd by strain GZ-22 isolated from mine soil based on biosorption and microbially induced carbonate precipitation. Environ. Sci Pollut Res., 2017, Vo. 24: 372-380.
EP23175806.1 Extended European Search Report dated Dec. 6, 2023.

\* cited by examiner

BIOCEMENTATION METHOD AND SYSTEM

REFERENCE TO RELATED APPLICATIONS

This application is a continuation application of U.S. patent application Ser. No. 16/153,374, filed Oct. 5, 2018, which claims priority to U.S. Provisional Application No. 62/568,539, filed Oct. 5, 2017, U.S. Provisional Application No. 62/577,911, filed Oct. 27, 2017, and U.S. Provisional Application No. 62/735,060, filed Sep. 22, 2018, the entirety of each of which is specifically and entirely incorporated by reference.

RIGHTS IN THE INVENTION

This invention was made with support from the United States Government under grant No. HR001117C0077, awarded by the Defense Advanced Research Project Agency, and, accordingly, the United States Government has certain rights in this invention.

BACKGROUND

1. Field of the Invention

The invention is directed to kits, compositions, tools and methods comprising a cyclic process for forming biocement in natural environments. In particular, the invention is directed to materials and methods for converting nitrogen and carbon and/or nitrogenous and carbon compounds into urea, which is then utilized to form biocement in calcium containing waters.

2. Description of the Background

Global industrial production of ammonia in 2014 was 176 million tons, a 16% increase over the 2006 production of 152 million tons. Industrial ammonia production is responsible for 1.44% of global CO2 emissions. Ammonia production consumes 5% of global natural gas production, and consumes about 2% of global energy production.

The biocementation reaction (see FIG. 1) relies on the metabolic hydrolysis of urea, producing ammonium and carbonate ions in a solution containing calcium chloride.

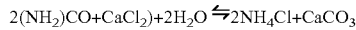

Calcium cations react with the carbonate anions at the surface of the bacterial membrane, forming calcium carbonate of the polymorph calcite. Ammonium cations and chloride anions remain in balance in the process water.

Calcium chloride is produced by reacting calcium oxide with ammonium chloride to produce calcium chloride, water, and ammonia gas.

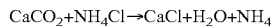

The Solvay process or ammonia-soda process is an industrial process for the production of sodium carbonate, also referred to as soda ash, and calcium chloride. The chemical process can be written as:

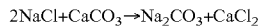

Ingredients for this process are readily available and include salt and limestone. Solvay-based chemical plants now produce roughly three-quarters of the world-wide supply, with the remainder provided from natural deposits.

Urea production, also called the Bosch-Meiser urea process after its discoverers, involves two main equilibrium reactions with incomplete conversion of the reactants. The first is carbamate formation: the fast exothermic reaction of liquid ammonia with gaseous carbon dioxide (CO2) at high temperature and pressure to form ammonium carbamate:

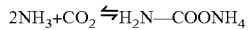

The second is urea conversion: the slower endothermic decomposition of ammonium carbamate into urea and water:

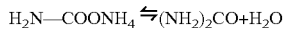

The overall conversion of $NH_3$ and $CO_2$ to urea is exothermic, the reaction heat from the first reaction driving the second. Like all chemical equilibria, these reactions behave according to Le Chatelier's principle, and the conditions that most favor carbamate formation have an unfavourable effect on the urea conversion equilibrium. Therefore, conventional process conditions involve a compromise: the ill-effect on the first reaction of the high temperature (around 190 C) needed for the second is compensated for by conducting the process under high pressure (140-175 bar), which favors the first reaction.

Although typically necessary to compress gaseous carbon dioxide to this pressure, the ammonia is available from the ammonia plant in liquid form, which can be economically pumped into the system. As urea conversion is incomplete, the product is separated from unchanged ammonium carbamate.

In urea production plants this was done by letting down the system pressure to atmospheric to let the carbamate decompose back to ammonia and carbon dioxide. Originally, because it was not economic to recompress the ammonia and carbon dioxide for recycle, the ammonia at least would be used for the manufacture of other products, for example ammonium nitrate or sulfate which vented the carbon dioxide as waste. Later process schemes made recycling unused ammonia and carbon dioxide practical. This was accomplished by depressurizing the reaction solution in stages (first to 18-25 bar and then to 2-5 bar) and passing it at each stage through a steam-heated carbamate decomposer, recombining the resultant carbon dioxide and ammonia in a falling-film carbamate condenser and pumping the carbamate solution into the previous stage.

SUMMARY OF THE INVENTION

The present invention overcomes problems and disadvantages associated with current strategies and designs, and provides new tools, compositions, and methods for process for forming biocement in natural environments.

One embodiment of the invention is directed to methods comprising: loading a solid object with urease-producing organisms and urea-producing organisms; placing the solid object into an environment containing one or more of carbon, nitrogen and calcium; and forming calcium carbonate within the solid object. Preferably loading with the urease-producing organisms and/or the urea-producing organisms comprises combining the solid object with dry organisms such that the organisms are retained within or on a surface of the solid object, or placing the solid object in a composition containing the urease-producing organisms and/or the urea-producing organisms. Preferably the solid object is loaded with spores and/or vegetative cells of the urease-producing organisms and/or the urea-producing organisms. Preferably the solid object comprises a natural or non-natural material, recycled or manufactured sand, ore, a brick, a block, masonry, a panel, tile, a board, rock, stone, crushed rock, crushed stone, minerals, crushed or fractured glass, wood, jute, ash, foam, basalt, fibers, mine tailings, paper, waste materials, waste from a manufacturing process, plastics, polymers, roughened materials, and/or combinations thereof, and also preferably, the solid object is permeable to microorganisms. Preferably, the solid object contains one or more of carbon, nitrogen and calcium, and more preferably the environment and the solid object contain sufficient quantities of carbon, nitrogen and calcium for forming calcium carbonate. Preferably, placing comprises immersing the solid object entirely within the environment. Preferably, the environment comprises an environment that promotes the proliferation of the urease-producing organisms and/or the urea-producing organisms a marine environment and more preferably is a marine environment. Preferably the urea-producing organisms comprise *Pseudomonas, Delaya avenusta, Thiosphaera pantotropha, Pseudomonas stutzen, Fragilaria crotonensis, Pseudoalteromonas* spp., *Pseudoalteromonas haloplanktis, Halomonas venusta, Pseudomonas balearica, Pseudomonas stutzeri, Bacillus megaterium. Exiguobacterium aurantiacum, Pseudoalteromonas aliena, Pseudoalteromonas luteoviolacea, E. coli*, and variants, serotypes, mutations, recombinant forms, and combinations thereof, and the urease-producing organisms comprise *Sporosarcina* spp., *S. pasteurii, S. ureae, Proteus* spp., *P. vulgaris, P. mirabilis, Bacillus* spp., *B. sphaericus, B. megaterium, Myxococcus* spp., *M. xanthus, Helicobacter* spp., *H. pylori*, and variants, serotypes, mutations, recombinant forms, and combinations thereof. Preferably the calcium carbonate is formed from a combination of urea produced by the urea-producing organisms that is acted upon by urease produced by the urease-producing organisms, and in the presence of carbon, nitrogen and calcium. Preferably the calcium carbonate is formed as a coating around the solid object (e.eg, as a biofilm containing organisms and calcium carbonate), and/or is formed outside of the solid object. Preferably the solid object containing calcium carbonate is utilized for erosion control in the environment, as a solid support of a structure within the environment, wherein the structure comprises building material, an electronic device, and/or a container. Preferably calcium carbonate is formed within, around, and/or external to the solid object for a period of six months or more, for a period of one year or more, or for a period of 5 years or more.

Another embodiment of the invention is directed to solid objects containing urease-producing organisms and urea-producing organisms, preferably containing calcium carbonate. Preferably the urease-producing organisms and the urea-producing organisms are viable, and preferably the urease-producing organisms produce urease and the urea-producing organisms produce urea. Preferably the urease and the urea in the presence of carbon, calcium and nitrogen form calcium carbonate. Preferably the solid object comprises a natural or non-natural material, recycled or manufactured sand, ore, a brick, a block, masonry, a panel, tile, a board, rock, stone, crushed rock, crushed stone, minerals, crushed or fractured glass, wood, jute, ash, foam, basalt, fibers, mine tailings, paper, waste materials, waste from a manufacturing process, plastics, polymers, roughened materials, and/or combinations thereof. Preferably the solid object further contains supplemental materials such as, for example, organic or inorganic material, rock, glass, wood, paper, metal, plastic, polymers, fibers, minerals or combinations thereof.

Another embodiment of the invention is directed to compositions comprising a viable mixture of urease-producing organisms and urea-producing organisms. Preferably the compositions contain the urease-producing organisms and the urea-producing organisms are in the form or spores and/or vegetative cells. Preferably the composition is aqueous or dry.

Other embodiments and advantages of the invention are set forth in part in the description, which follows, and in part, may be obvious from this description, or may be learned from the practice of the invention.

DESCRIPTION OF THE INVENTION

Biocementation involves the metabolic hydrolysis of urea, producing ammonium and carbonate ions in a solution containing calcium chloride. Calcium cations react with the carbonate anions at the surface of the bacterial membrane, forming calcium carbonate of the polymorph calcite. Ammonium cations and chloride anions remain in balance in the process water.

The invention is directed to the surprising discovery that this reaction can become cyclical. In one alternative, calcium carbonate is decomposed into calcium oxide and carbon dioxide at an elevated temperature. Calcium oxide reacts with ammonium chloride to form calcium chloride, water, and ammonia gas. The ammonia gas and carbon dioxide are reacted to synthesize urea and water which are then utilized in the biocementation process. In another alternative, calcium carbonate is decomposed, preferably at an elevated temperature or with acid, to form calcium oxide and carbon dioxide; reacting calcium dioxide with ammonium in a process to form urea and water; and reacting urea and calcium chloride to form biocement. Accordingly, depending on the precursor ingredients, the result can be the production of calcium carbonate, ammonia, ammonium chloride, calcium chloride, urea, and/or ammonia. Preferably reacting urea with calcium chloride further forms ammonium chloride. Preferably, ammonium chloride is further decomposing to form acid and ammonia.

Figure 1:
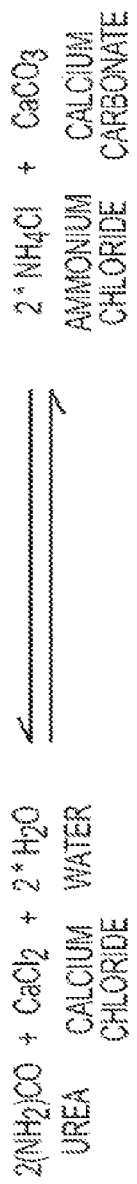
FIG. 1 The urea-hydrolysis biocementation reaction.
Figure 2:
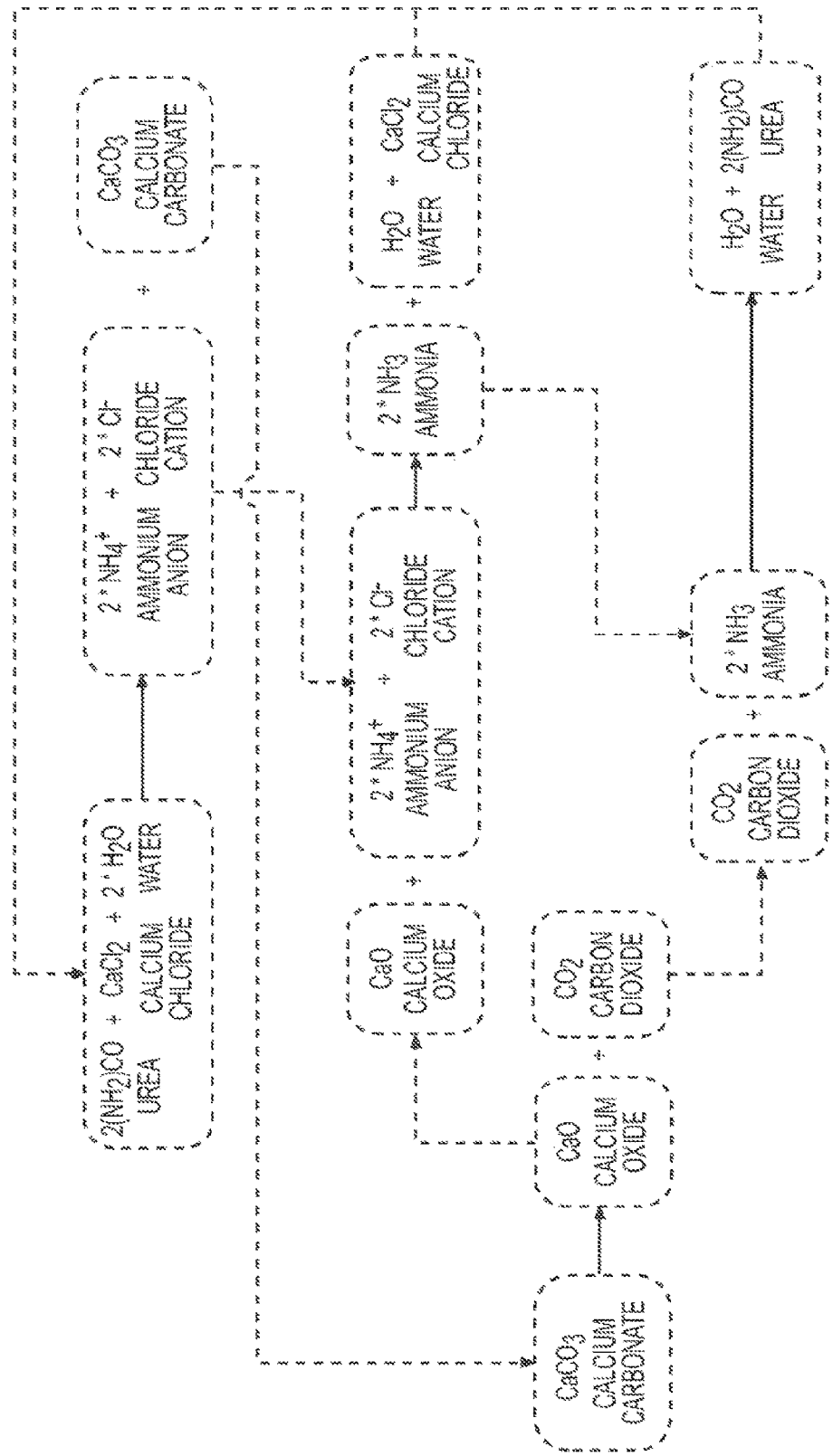
FIG. 2 The urea-hydrolysis biocementation reaction as a closed loop industrial cyclic process.
Figure 3:
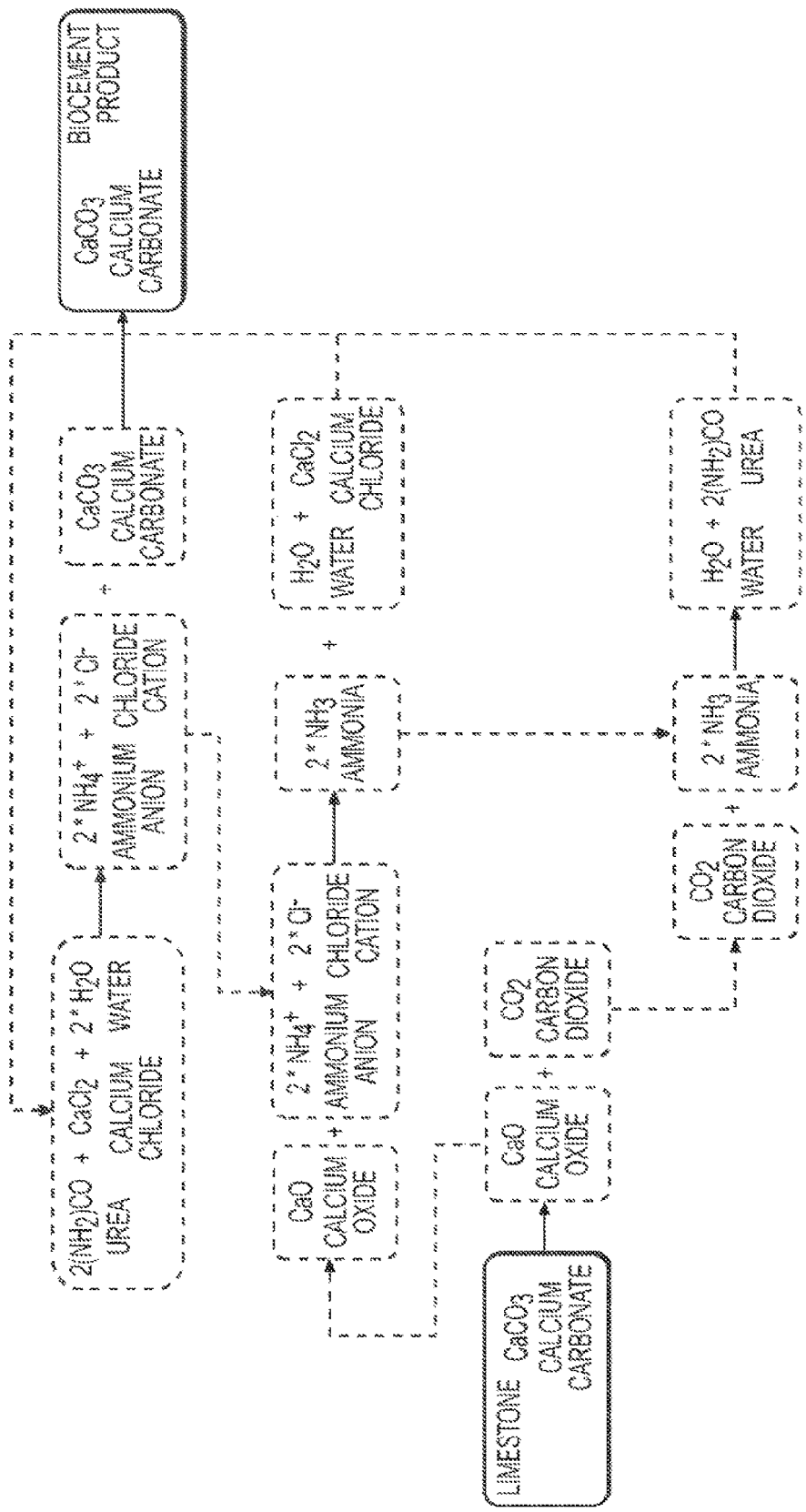
FIG. 3 The urea-hydrolysis biocementation reaction as an industrial cyclic process where limestone calcium carbonate is converted into biocement.

The cyclic process can be achieved using existing industrial processes combined with biocementation technologies (see e.g., FIG. 2). As the resulting product can be for the formation of biocement as a building material, an equivalent input stream of calcium carbonate provides fuel to the process cycle (see FIG. 3). At a large industrial scale, an input source of calcium carbonate is mined limestone deposits, as are currently used in the manufacture of Portland Cement. Preferably decomposing comprises treating calcium carbonate with elevated temperatures or an acid wherein the preferred elevated temperature is about 600° C. or more, 700° C. or more, 800° C. or more, 850° C. or more, 900° C. or more, 1,000° C. or more, or even higher temperatures. The preferred acid comprises hydrochloric acid although a variety of acids may be utilized including, but not limited to phosphoric acid, nitric acid, acetic acid and combinations thereof. Preferably the process comprises elevated pressure such as, for example, greater than 100 psig, greater than 200 psig, greater than 300 psig, greater than 400 psig, greater than 500 psig, or greater. Corona discharge may also be utilized or co-culture with urea-producing organisms. A corona discharge is an electrical discharge brought on by the ionization of a fluid such as air surrounding a conductor that is electrically charged. A corona will occur when the strength (potential gradient) of the electric field around a conductor is high enough to form a conductive region, but not high enough to cause electrical breakdown or arcing to nearby objects. It is often seen as a bluish (or other color) glow in the air adjacent to pointed metal conductors carrying high voltages, and emits light by the same property as a gas discharge lamp. This step can be performed in isolation for the production of bulk urea, or can be employed within the aggregate matrix for localized urea production, consumed at the time of biocementation.

Another embodiment is to co-culture with urea-producing organisms such as, for example, by the autotrophic metabolism of atmospheric nitrogen and carbon dioxide into urea or by the bacterial decomposition of organic matter. Urea-producing microrganisms include, for example, various species of *Pseudomonas, Delaya avenusta, Thiosphaera pantotropha, Pseudomonas stutzeri, Fragilaria crotonensis, Pseudoalteromonas* sp., *Pseudoalteromonas haloplanktis, Halomonas venusta, Pseudomonas balearica, Pseudomonas stutzeri, Bacillus megaterium. Escherichia coli, Exiguobacterium aurantiacum, Pseudoalteromonas aliena, Pseudoalteromonas luteoviolacea*, variants, serotypes, mutations, recombinant forms, or combinations thereof, and other organisms and microorganisms known to those of ordinary skill in the art.

Modern dry-process Portland Cement manufacturing utilizes a heat source of 1,850° C. to 2,000° C. for achieving a material sintering temperature of 1,450 aC within a rotary kiln. Early in the manufacturing process, calcium carbonate is decomposed into calcium oxide and carbon dioxide at a temperature of 850° C. in a preheater/calciner tower, where the required heat energy is provided through partial recovery of the rotary kiln exhaust. A calcium oxide digester, implemented as a side-chain process at a Portland Cement manufacturing plant, could be similarly fueled by the unused waste heat energy from the cement rotary kiln to process on-site calcium carbonate. The calcium oxide, reacted with ammonium chloride, produces calcium chloride, water, and ammonia gas. The ammonia gas then reacted with carbon dioxide released during the side-chain calcium oxide production produces urea and water as a carbon neutral materials recycling process. The inputs of this process are thereby ammonium chloride and calcium carbonate, with the output materials of calcium chloride and urea.

Figure 4:
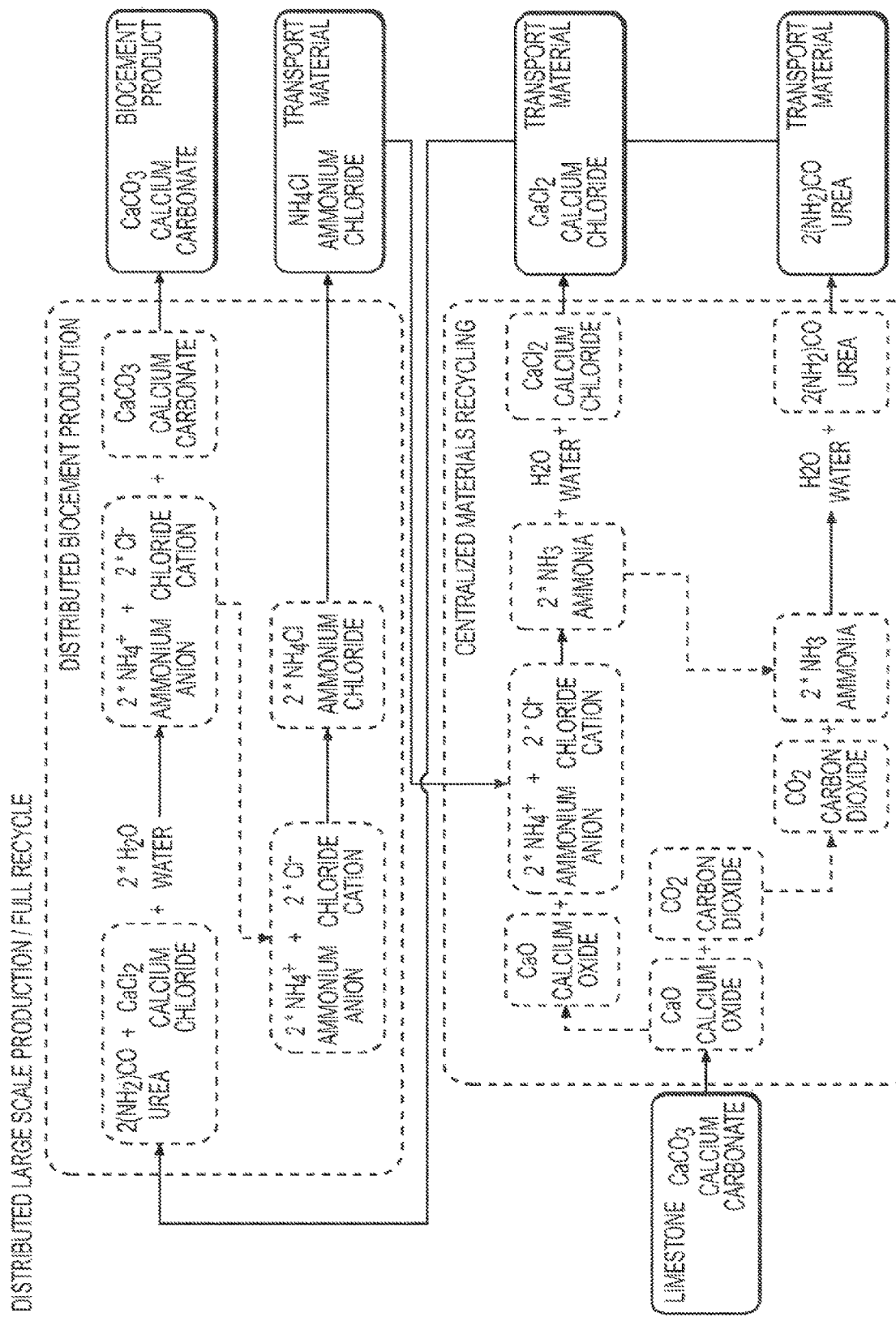
FIG. 4 The urea-hydrolysis biocementation reaction represented at large-scale industrial production volumes.
Figure 5:
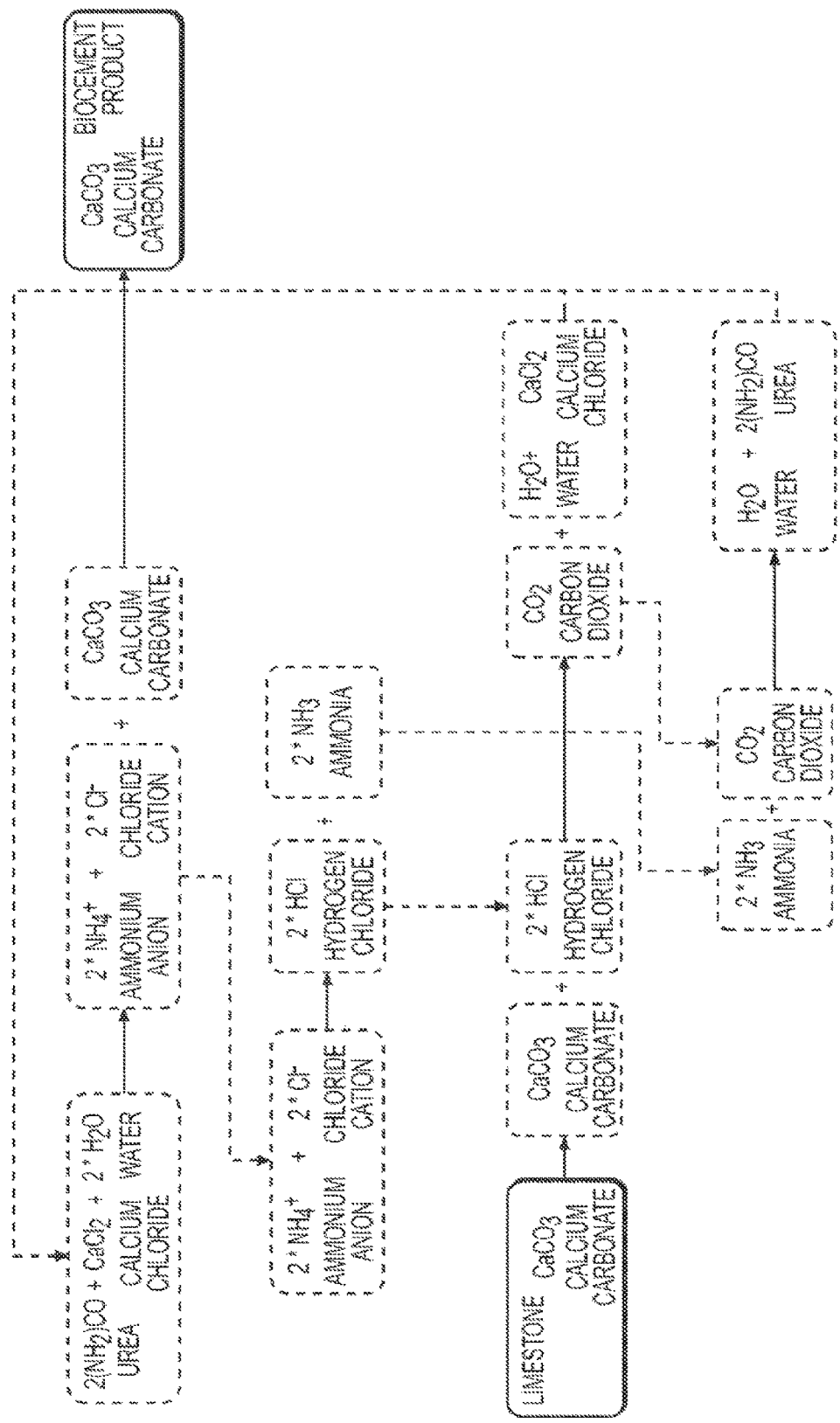
FIG. 5 The urea-hydrolysis biocementation reaction.
Figure 6:
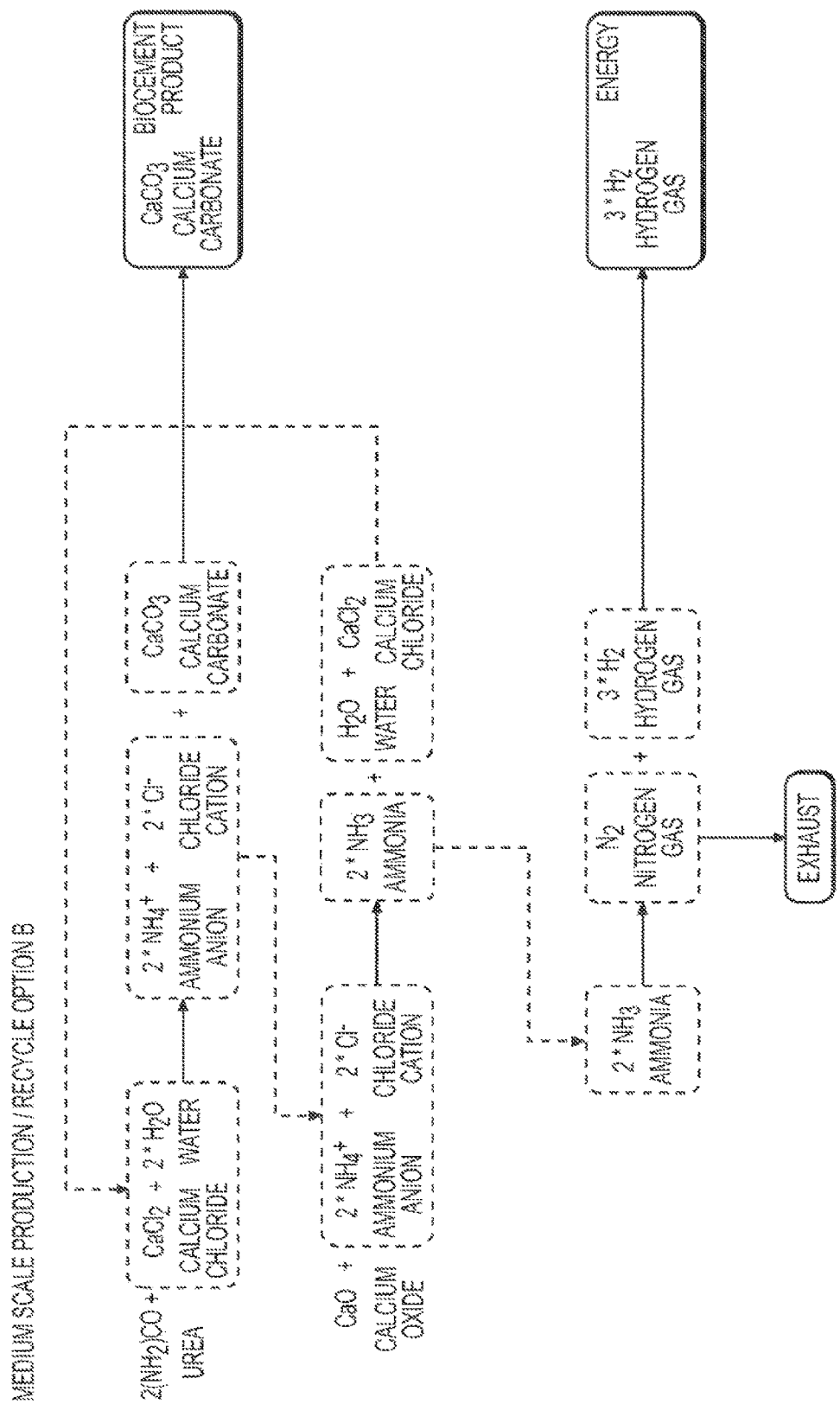
FIG. 6 The urea-hydrolysis biocementation reaction where process water is recycled through the regeneration of calcium chloride, and the electrolysis of ammonia into hydrogen and nitrogen gases.

In this large scale model of the urea-hydrolysis biocementation reaction, industrial production volumes are indicated whereby limestone input material is converted into biocement products (see FIG. 4). The metabolic biocementation process is represented as a distributed model, where ammonium chloride, urea, and calcium chloride are used as stable, soluble materials for transport to and from an industrial materials recycling system whereby materials are centralized in a recycling plant that provides distributed biocement production facilities with urea and calcium chloride for the production of biocement construction materials using local aggregates. Ammonium chloride recovered from the distributed biocement production streams is returned to the centralized materials recycling plant. This closes the loop by reproducing and redistributing fresh calcium chloride and urea. Calcium chloride and urea represent approximately 75% of the total direct material cost. This large scale model moves the supply chain of these important materials, where the direct costs are internally determined by operational costs of the centralized materials recycling plant, rather than market prices from a third party supplier.

Biocement production targets implementation of the full-recycle, large scale process models have been initially determined by current scales of industrial urea synthesis. Urea plants are most commonly coupled with ammonia production plants, where the carbon dioxide released during ammonia production is reacted with a fraction of the produced ammonia for the formation of urea. A small, modern urea plant produces approximately 350,000 tons of urea per year. Based on the biocement production input material ratio of 1 mol. urea ($2NH_2CO$):1 mol. calcium chloride ($CaCl_2$), a production of 350,000-tons urea requires a corresponding production of 326,791-tons calcium oxide (see Table 1). An efficient US Portland Cement manufacturing plant produces over 2,000,000-tons of cement per year, consuming more than 1,276,200-tons calcium oxide.

TABLE 1

Comparative mass of process materials in large-scale model. Assumes an annual urea production of 350,000-tons.

| Material | Molar Mass | Molar Ratio | Production Mass |
| --- | --- | --- | --- |
| Urea | 60.06 g/mol | 1 | 350,000 tons |
| Calcium Chloride | 110.98 g/mol | 1 | 646,737 tons |
| Calcium Carbonate | 100.09 g/mol | 1 | 583,257 tons |
| Calcium Oxide | 56.08 g/mol | 1 | 326,791 tons |
| Carbon Dioxide | 44.01 g/mol | 1 | 256,469 tons |
| Ammonium Chloride | 53.49 g/mol | 2 | 623,438 tons |
| Ammonia | 17.03 g/mol | 2 | 198,497 tons |

Accordingly, the system can be designed for the large (or small scale) production of one or more of calcium carbonate, calcium oxide, calcium chloride, ammonium chloride, ammonia, and urea.

Another embodiment of the invention is directed to an industrial cyclic process. For example, the industrial cyclic process is preferably for the production of biocement material, where calcium ions and dissolved carbon dioxide/carbonates are provided by seawater, industrial waste streams, and/or naturally occurring brines. Co-culture organism group (1) produces urea from the carbon and a nitrogen substrate. Co-culture organism group (2) produces biocement using seawater calcium ions and organism group (1) produced urea. Organism group (2) produced ammonium is then used by organism group (1) as the nitrogen substrate for urea production.

The industrial process is also preferably for the production of urea and/or ammonia for use in agriculture, chemical, and manufacturing industries, where an organism or consortia of organisms produce urea from a nitrogen substrate and a carbon rich media. Produced urea can be separated and used in aqueous form, or dried into solids such as pellets, prills, or powders for downstream use. A subsequent step using a urease producing-bacteria can hdyrolyze the urea into ammonium, which is separated as ammonia liquor or compressed ammonia gas for downstream use. Examples of urease-producing bacteria include, but are not limited to *Sporosarcina* spp. (e.g., *S. pasteurii* and *S. ureae*), *Proteus* spp. (e.g., *P. vulgaris* and *P. mirabilis*), *Bacillus* spp. (e.g., *B. sphaericus* and *B. megaterium*), *Myxococcus* spp (e.g., *M. xanthus*), *Helicobacter* spp. (e.g., *H. pylori*), or variants, serotypes, mutations, recombinant forms, or combinations thereof. Preferably the organism are vegetative cells, although spores can be utilized and converted to vegetative cells that produce urease, or the extracted urease enzyme may be used without the presence of the enzyme-producing organism. The nitrogen substrate for urea production comprises complex nitrogen sources, or gaseous atmospheric nitrogen depending on the specification of the consortia. Carbon can be supplied in any form and, for example, converted to a liquid as dissolved atmospheric carbon dioxide. The reaction may further comprise additional materials to be incorporated into the biocement such as, for example, organic or inorganic material, rock, glass, wood, paper, metal, plastic, polymers, fibers, minerals or combinations thereof Engineered Living Marine Cement (ELMc)

Another embodiment of the invention is directed to tools, compositions, production methods, and structures for engineered living marine cement (ELMc). ELMc involves the development of a living biological concrete and/or concrete-like materials that is utilized for marine and other applications. ELMc materials have the capacity to self-heal (e.g., maintenance free), mitigating common structural degradations to traditional marine concretes that result in significant maintenance and/or replacement costs. A viable ELMc material preferably sources materials for biocement formation directly from the environment (e.g., seawater, mine environments).

Preferably, ELMc materials employ bacteria strains that are native to or adaptable to the environment in which the structure is produced. For example, in a marine environment, feedstock urea and calcium is sourced directly from seawater. While Calcium is plentiful in seawater as a mechanic of the oceanic carbon pump, urea is available in smaller amounts which may limit the rates of biocement formation. Oceanic urea as produced by zooplankton, marine life such as, for example, fish, and marine bacteria. For marine biocement structures, ELMc preferably involves a consortia of urea-producing and urease-producing bacteria. Over 300 strains of marine bacteria were screened for urea production and 24 were selected, which fell into seven distinct species. Strains were further developed by selection and/or genetic engineering resulting in a number of very high levels of ELMc production. Preferably, strains were developed for biocement formation in units during 7-day trials, using a synthetic seawater feedstock that includes no urea.

Preferred bacterial strains generate urea through two different metabolic pathways: (a) purine/pyramidine metabolism and (b) cleavage of the amino acid L-arginine by the enzyme arginase. In the marine environment, these substrates remain a limiting factor, where synthetic approaches enable the use of more plentiful carbon sources. For example, metabolic pathways are genetically engineered for the industrial production of L-arginine from a glucose carbon source. Similar tools and processes enable the utilization of alternative carbon sources, including those produced directly from dissolved inorganic carbon.

A preferred ELMc production involves the local production of urea by bacterial generation at the nucleation site of cement formation. This approach eliminates the reliance on industrially produced urea and removes urea as a feedstock component. ELMc developed synthetic biology tools and methods involves two processes and application conditions for industrial biocement products.

Firstly, ELMc produces biocement as a maintenance activity relevant to a material service life of years, decades, and longer. In this methodology, maintenance involves a gradual deposition of material into structural damages and defects, but maintenance begins immediately. Preferably, maintenance is a continuous process. Secondly, ELMc involves sourcing necessary feedstock components directly from nitrogen-limited natural sources such as seawater, in native concentrations, along with any other impurities or variable factors. The ELMc produced materials are comprised of a consortia of bacteria that generates organic urea at the site of calcium carbonate formation. Feedstocks are limited by components and/or concentrations found in natural seawaters. Sustainable biocement development, according to the disclosures herein, provide both a carbon accounting and guide life-cycle analysis (LCA) to provide sustainable sources for feedstock carbon, while maintaining the performance and commercial viability of established products.

Another embodiment of the invention is directed to methods comprising: loading a solid object with urease-producing organisms and urea-producing organisms; placing the solid object into an environment containing one or more of carbon, nitrogen and calcium; and forming calcium carbonate within the solid object. Preferably loading with the urease-producing organisms and/or the urea-producing organisms comprises combining the solid object with dry organisms such that the organisms are retained within or on a surface of the solid object, or placing the solid object in a composition containing the urease-producing organisms and/or the urea-producing organisms. Preferably the solid object is loaded with spores and/or vegetative cells of the urease-producing organisms and/or the urea-producing organisms. Preferably the solid object comprises a natural or non-natural material, recycled or manufactured sand, ore, a brick, a block, masonry, a panel, tile, a board, rock, stone, crushed rock, crushed stone, minerals, crushed or fractured glass, wood, jute, ash, foam, basalt, fibers, mine tailings, paper, waste materials, waste from a manufacturing process, plastics, polymers, roughened materials, and/or combinations thereof, and also preferably, the solid object is permeable to microorganisms. Preferably, the solid object contains one or more of carbon, nitrogen and calcium, and more preferably the environment and the solid object contain sufficient quantities of carbon, nitrogen and calcium for forming calcium carbonate. Preferably, placing comprises immersing the solid object entirely within the environment. Preferably, the environment comprises an environment that promotes the proliferation of the urease-producing organisms and/or the urea-producing organisms a marine environment and more preferably is a marine environment such as disclosed herein. Preferably the calcium carbonate is formed from a combination of urea produced by the urea-producing organisms that is acted upon by urease produced by the urease-producing organisms, and in the presence of carbon, nitrogen and calcium. Preferably the calcium carbonate is formed as a coating around the solid object (e.eg, as a biofilm containing organisms and calcium carbonate), and/or is formed outside of the solid object. Preferably the solid object containing calcium carbonate is utilized for erosion control in the environment, as a solid support of a structure within the environment, wherein the structure comprises, for example, building material, an electronic device, and/or a container. Preferably calcium carbonate is formed within, around, and/or external to the solid object for a period of six months or more, for a period of one year or more, or for a period of 5 years or more, or the calcium carbonate is self-replicating or self-sustaining and perpetual for the life of the solid object. In addition, such solid objects are also self-repairing.

Another embodiment of the invention is directed to solid objects containing urease-producing organisms and urea-producing organisms, preferably containing calcium carbonate. Preferably the urease-producing organisms and the urea-producing organisms are viable, and preferably the urease-producing organisms produce urease and the urea-producing organisms produce urea. Preferably the urease and the urea in the presence of carbon, calcium and nitrogen form calcium carbonate. Preferably the solid object comprises a natural or non-natural material, recycled or manufactured sand, ore, a brick, a block, masonry, a panel, tile, a board, rock, stone, crushed rock, crushed stone, minerals, crushed or fractured glass, wood, jute, ash, foam, basalt, fibers, mine tailings, paper, waste materials, waste from a manufacturing process, plastics, polymers, roughened materials, and/or combinations thereof. Preferably the solid object further contains supplemental materials such as, for example, organic or inorganic material, rock, glass, wood, paper, metal, plastic, polymers, fibers, minerals or combinations thereof.

Another embodiment of the invention is directed to compositions comprising a viable mixture of urease-producing organisms and urea-producing organisms. Preferably the compositions contain the urease-producing organisms and the urea-producing organisms are in the form or spores and/or vegetative cells. Preferably the composition is aqueous or dry.

The following examples illustrate embodiments of the invention, but should not be viewed as limiting the scope of the invention.

EXAMPLES

Example 1 Platform Adaptability

Traditional Portland Cement manufacturing involves a 20th-Century centralized industrial model, where the production of cement is tied to capital and energy intensive processes (e.g., methane fired tunnel kiln). With changes in market demands, regulatory conditions, material resources, and global understanding of environmental impacts evolve, the adaptation of traditional cement plants, there is a need for a change of infrastructural for the next plant to be built. The production design disclosed and described herein, fills that need and also provided an adaptable platform.

The production of biocement according to the disclosures here, involves two interrelated systems: manufacturing equipment, and the biotechnology of biocement production. Manufacturing equipment includes equipment for materials handling (e.g., mixing, forming, and transit equipment), and solid-state fermentation (e.g., feedstocks and delivery), representing hard capital costs for manufacturing product. A large portion of materials and infrastructure production includes bacteria and feedstock materials for manufacturing and provided to production sites.

A plant of this disclosure provides for adapting the feedstock chemicals required for biocement production, without also requiring significant infrastructural or capital changes to the manufacturing systems, or the need for a costly carbon source such as methane. This processes of this disclosure increases sustainability, extend performance, work with local feedstock components, reduce production costs, and is rapidly deployable.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A living construction material comprising:
 a loaded solid object comprising cells of a urease-producing organism and cells of a urea-producing organism, wherein the loaded solid object is loaded with spores and vegetative cells of the urease-producing organism and the urea-producing organism via placement of a solid object in a composition containing dry organisms such that the organisms are retained within or on a surface of the solid object; and
 a carbon source, a nitrogen source and a calcium source, wherein the loaded solid object is configured to form calcium carbonate within, around, or external to the loaded solid object for a period of six months or more using the cells of the urease-producing organism and the urea-producing organism, and the carbon, nitrogen and calcium sources, while the loaded solid object is immersed entirely within a marine environment.

2. The living construction material of claim 1, wherein the loaded solid object comprises recycled or manufactured sand, ore, a brick, a block, masonry, a panel, tile, a board, rock, stone, crushed rock, crushed stone, minerals, crushed or fractured glass, wood, jute, ash, foam, basalt, fibers, mine tailings, paper, waste materials, waste from a manufacturing process, plastics, polymers, roughened materials, or combinations thereof.

3. The living construction material of claim 2, further containing supplemental materials.

4. The living construction material of claim 3, wherein the supplemental materials comprise organic or inorganic material, rock, glass, wood, paper, metal, plastic, polymers, fibers, minerals or combinations thereof.

5. The living construction material of claim 1, wherein the loaded solid object is permeable to microorganisms.

6. The living construction material of claim 1, wherein the urea-producing organism comprises *Pseudomonas, Delaya avenusta, Thiosphaera pantotropha, Pseudomonas stutzen, Fragilaria crotonensis, Pseudoalterornonas* spp., *Pseudoalteromonas haloplanktis, Halomonas venusta, Pseudomonas balearica, Pseudomonas stutzeri, Bacillus megaterium, Escherichia coli, Exiguobacterium aurantiacum, Pseudoalteromonas aliena, Pseudoalteromonas luteoviolacea*, or variants, serotypes, mutations, recombinant forms, or combinations thereof.

7. The living construction material of claim 6, wherein the urease-producing organism comprises *Sporosarcina* spp., *S. pasteurii, S. ureae, Proteus* spp., *P. vulgaris, P. mirabilis, Bacillus* spp., *B. sphaericus, B. megaterium, Myxococcus* spp., *M xanthus, Helicobacter* spp., *H. pylori*, or variants, serotypes, mutations, recombinant forms, or combinations thereof.

8. The living construction material of claim 1, wherein calcium carbonate is formed within, around, or external to the loaded solid object for a period of one year or more when the loaded solid object is placed in the marine environment.

9. The living construction material of claim 1, wherein calcium carbonate is formed within, around, or external to the loaded solid object for a period of 5 years or more when the loaded solid object is placed in the marine environment.

10. A method of construction comprising placing one or more living construction materials of claim 1 in the marine environment.

11. The method of claim 10, wherein the marine environment comprises an environment that promotes the proliferation of the urease-producing organism or the urea-producing organism.

12. The method of claim 11, wherein the calcium carbonate is formed from a combination of urea produced by the urea-producing organism that is acted upon by urease produced by the urease producing organism, and in the presence of carbon, nitrogen and calcium.

13. The method of claim 12, wherein the calcium carbonate is formed as a coating around the loaded solid object.

14. The method of claim 13, wherein the solid object containing calcium carbonate is utilized for erosion control in the environment.

15. The method of claim 13, wherein the solid object containing calcium carbonate is utilized as a solid support of a structure within the environment.

16. The method of claim 15, wherein the structure comprises building material, an electronic device, or a container.

* * * * *